(12) United States Patent
Miwa et al.

(10) Patent No.: US 6,394,603 B2
(45) Date of Patent: May 28, 2002

(54) OPHTHALMIC APPARATUS

(75) Inventors: Tetsuyuki Miwa; Nobuo Suzuki, both of Aichi; Munehiro Nakao, Toyokawa, all of (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/810,484

(22) Filed: Mar. 19, 2001

(30) Foreign Application Priority Data

Mar. 22, 2000 (JP) .......................................... 2000-081046

(51) Int. Cl.$^7$ ................................................ A61B 3/10
(52) U.S. Cl. ...................................................... 351/215
(58) Field of Search ................................ 351/200, 205, 351/214, 215, 216, 221; 356/491, 495, 496, 497; 600/476

(56) References Cited

U.S. PATENT DOCUMENTS

| | | | |
|---|---|---|---|
| 4,747,683 A | 5/1988 | Doane | |
| 5,293,535 A | 3/1994 | Sensui | |
| 5,719,659 A | 2/1998 | Suzuki | |
| 5,973,781 A | * 10/1999 | Moeller et al. | 356/495 |
| 6,027,216 A | * 2/2000 | Guyton et al. | 351/200 |
| 6,236,459 B1 | * 5/2001 | Negaharipour et al. | 356/496 |

FOREIGN PATENT DOCUMENTS

| | | |
|---|---|---|
| EP | 1 029 504 A1 | 8/2000 |
| JP | 62-222143 | 9/1987 |
| JP | 5-154106 | 6/1993 |
| JP | 7-136120 | 5/1995 |
| JP | 8-52112 | 2/1996 |
| JP | 8-103413 | 4/1996 |
| JP | 10-33483 | 2/1998 |
| JP | 2000-237135 | 9/2000 |

* cited by examiner

*Primary Examiner*—George Manuel
(74) *Attorney, Agent, or Firm*—Oliff & Berridge PLC

(57) ABSTRACT

An ophthalmic apparatus for observing an eye to be examined is disclosed. This apparatus includes an observation optical system including an objective lens, for observing the eye through the objective lens; an illumination optical system including an illumination light source, for illuminating the eye through the objective lens; a polarization beam splitter having a property of transmitting one of linear polarized light beams that mutually perpendicularly intersect, and reflecting another linear polarized light beam, the polarization beam splitter being disposed opposite to the eye to be examined with respect to the objective lens, whereby aligning optical paths of the illumination and observation optical systems in a mutually coaxial relation; and a ¼ wave plate disposed between the objective lens and the eye to be examined.

6 Claims, 2 Drawing Sheets

OPHTHALMIC APPARATUS

BACKGROUND OF THE INVENTION

1. Field of the Invention

The present invention relates to an ophthalmic apparatus for observing an eye to be examined.

2. Description of Related Art

As ophthalmic apparatus for observing an eye to be examined, there have been known ophthalmic apparatus and others for observing interference fringes formed by a lacrimal layer on a cornea of the examinee's eye, for example, to diagnose dry eye or the like.

However, such the prior art apparatus have a problem that flare would occur in an observation image, i.e., an image of the eye to be examined, and various problems caused by structures for preventing the occurrence of flare, or removing the flare. For instance, there is an apparatus in which polarizing plates are arranged in an illumination optical system and an observation optical system, respectively, of which optical paths are aligned coaxially to each other by a half-mirror, thereby preventing the occurrence of flare. This apparatus however includes a problem that fine positional adjustment to the polarizing plates is needed so that the direction of each polarization axis of the plates becomes proper. In addition, a quantity of light received by an imaging device such as a CCD camera or the like for observing, or photographing an image of an eye to be examined, would be reduced by the use of the half-mirror.

SUMMARY OF THE INVENTION

The present invention has been made in view of the above circumstances and has an object to overcome the above problems and to provide an ophthalmic apparatus with a simple structure capable of preventing the occurrence of flare and efficiently illuminating an eye to be examined.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic apparatus for observing an eye to be examined, the apparatus including: an observation optical system including an objective lens, for observing the eye through the objective lens; an illumination optical system including an illumination light source, for illuminating the eye through the objective lens; a polarization beam splitter having a property of transmitting one of linear polarized light beams that mutually perpendicularly intersect, and reflecting another linear polarized light beam, the polarization beam splitter being disposed opposite to the eye to be examined with respect to the objective lens, whereby aligning optical paths of the illumination and observation optical systems in a mutually coaxial relation; and a ¼ wave plate disposed between the objective lens and the eye to be examined.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of an ophthalmic apparatus embodying the present invention will now be given referring to the accompanying drawings. In this embodiment, explanation is made on an ophthalmic apparatus for diagnosing dry eye and the like by observing interference fringes formed by a lacrimal layer on a cornea of an eye to be examined.

Figure 3:
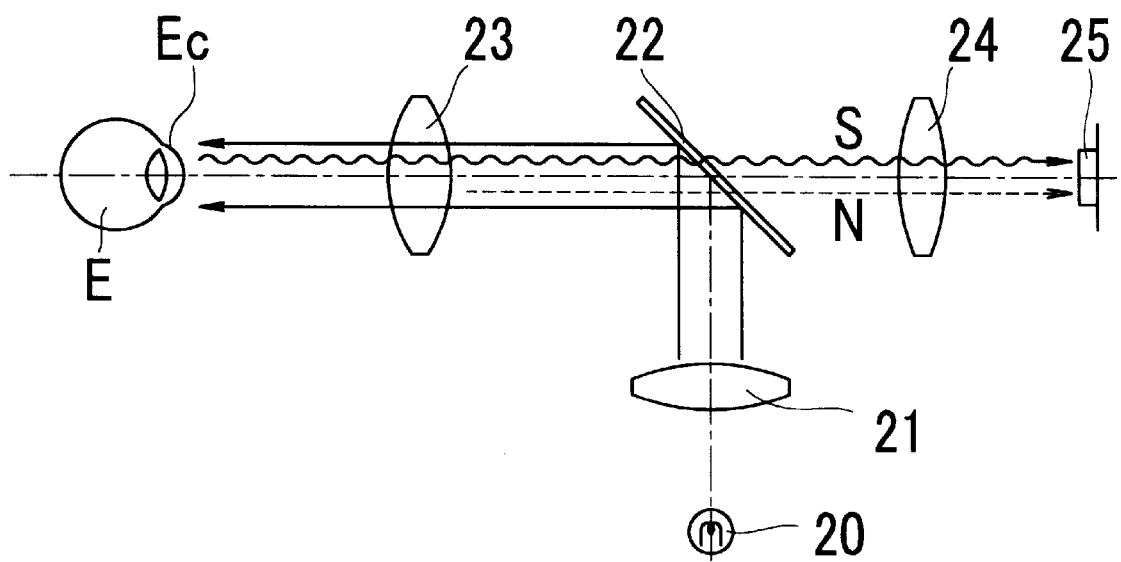
FIG. 3 is a schematic view of an optical system of an ophthalmic apparatus in a prior art.

Prior to explanation of the apparatus of the invention, a prior art apparatus of the same kind is mentioned below. FIG. 3 is a schematic view of an optical system of the prior art apparatus of the same kind as that of the invention. Illumination light emitted from an illumination light source 20 passes through a projection lens 21 and then is reflected by a half-mirror 22, as indicated by a sold line in FIG. 3, toward an eye E to be examined, thereby illuminating the eye E through an objective lens 23. Reflected light from a lacrimal layer on a cornea Ec of the eye E goes as a signal light beam S (a wavy line in FIG. 3) through the lens 23, the half-mirror 22, and an image-forming lens 24, and falls on an imaging face of a CCD camera 25. The images of interference fringes formed by the lacrimal layer are imaged by the camera 25 and displayed on a monitor not illustrated. An examiner can thus diagnose the eye E based on the images of interference fringes displayed.

In the above case, however, a part of the illumination light is reflected from the back side of the lens 23, opposite to the eye E, forming a disturbance light beam N (a dotted line in FIG. 3) which is incident on the camera 25 in a mixed state with the signal light beam S. This disturbance light beam N may become flare, causing unclear or blurred contrast of the interference fringe images, thereby making it difficult to diagnose the eye E.

To solve the above problems, an apparatus for preventing the occurrence of flare has been proposed as disclosed in Japanese Patent Unexamined Publication No. 8-52112. In this apparatus, two polarizing plates having different polarization directions (polarization axes) are arranged in an illumination optical system and an observation optical system, of which respective optical paths are made coaxial by a half-mirror. A ¼ wave plate is further disposed between the objective lens and the eye to be examined. The polarization direction of an illumination light (and a reflected light from the objective lens) and the polarization direction of a corneal reflection light are perpendicular to each other. Thus, the occurrence of flare is reduced.

In the above apparatus, however, the polarizing plates disposed in the illumination and observation optical systems respectively have to be adjusted precisely so that the polarization axes are correctly perpendicular to each other. For this purpose, it requires much time and labor for optical adjustment and the like during manufacture of the apparatus. Furthermore, due to the use of the half-mirror, the quantity of light received by the CCD camera for observation (or for imaging of the eye to be examined) is reduced to about one-fourth the light quantity emitted from a light source of the illumination optical system. To obtain sufficient light quantity, therefore, there is also a problem that a large-sized illumination light source is required for increase of the output power.

The apparatus according to the present invention developed for solving the above problems is constructed that a polarization beam splitter having the property of permitting one of linear polarized light beams that mutually perpendicularly intersect to pass therethrough, and reflecting another linear polarized light beam, is placed opposite to the examinee's eye with respect to the objective lens, so that respective optical paths of the illumination and observation optical systems are aligned coaxially to each other, and also a ¼ wave plate is disposed between the objective lens and the examinee's eye. Thus, the polarization direction of the illumination light beam (and a reflected light beam from the objective lens) and the polarization direction of a corneal reflection light beam mutually perpendicularly intersect, thereby preventing the occurrence of flare. With such the structure, the problems that a time and labor needed for adjustment of the polarizing plates and an insufficient quantity of light can be solved.

It is to be noted that U.S. Pat. No. 5,293,535 (corresponding to Japanese Patent Unexamined Publication No. 5-154106) discloses the use of a polarization beam splitter whereby optical paths of a light projecting optical system and a light receiving optical system are aligned mutually coaxially. However, this is aimed at detecting a light quantity of a Purkinje image in a photographing camera for general use. Accordingly, the entire optical system and the object to be photographed completely differ from the optical system of the invention (the optical system for observing or photographing the eye to be examined, in particular, an anterior portion of the eye) and the object (the eye to be examined, in particular, the anterior eye portion) to be observed or imaged. In other words, the apparatus proposed in the publication '535 and the present invention are included in different technical fields.

Figure 1:
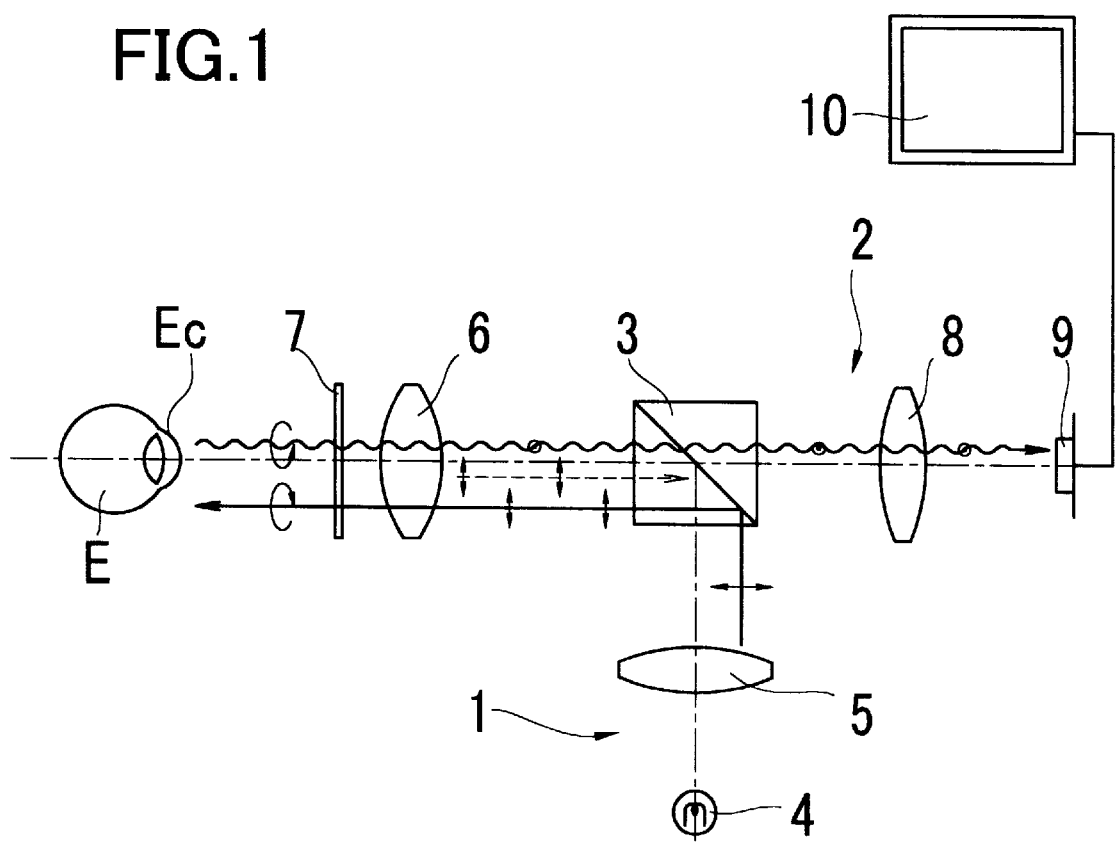
FIG. 1 is a schematic view of an optical system of an ophthalmic apparatus in an embodiment according to the present invention.

Next, the apparatus of the present invention is explained below. FIG. 1 is a schematic view of an optical system of an ophthalmic apparatus in the present embodiment, which also schematically shows a polarized condition of each luminous flux.

Figure 2:
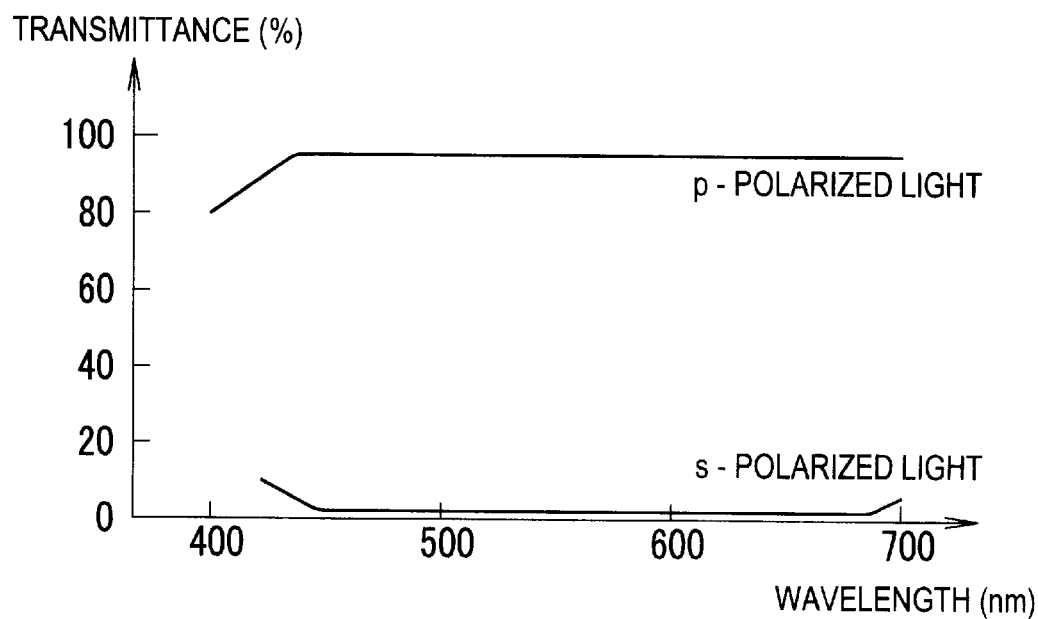
FIG. 2 is a graph showing ophthalmic characteristics of a polarization beam splitter in the embodiment.

An illumination optical system 1 and an observation optical system 2 are arranged so that respective optical paths are aligned mutually coaxially by a polarization beam splitter 3. This beam splitter 3 has the property of permitting one of linear polarized light beams that mutually perpendicularly intersect to pass therethrough, and reflecting another. Thus, the transmitted light and the reflected light become linear polarized light beams that perpendicularly intersect. As the polarization beam splitter 3 in the present embodiment, a wide frequency band polarization beam splitter having the property of transmitting most of p-polarized light component (i.e., the light polarized in a vertical direction to the drawing sheet) of light of wavelengths in a wide visible region; about 450 to 680 nm, and reflecting most of s-polarized light component (i.e., the light polarized in a parallel direction to the drawing sheet), as shown in FIG. 2.

Illumination light emitted from a white light source 4 such as a halogen lamp or the like passes through a projective lens 5 and is incident on the polarization beam splitter 3. Among the illumination light made incident on the beam splitter 3, most of the s-polarized light component in the visible region is reflected by the beam splitter 3 toward the eye E to be examined. On the other hand, the p-polarized light component of the illumination light is transmitted through the beam splitter 3 and absorbed in an absorber not illustrated.

The illumination light of the s-polarized light reflected toward the eye E is transmitted through the objective lens 6 and is incident on a ¼ wave plate 7 having the property of converting linear polarized light to circularly polarized light. The illumination light of the s-polarized light made incident on the ¼ wave plate 7 is converted to for example a clockwise circularly polarized light, thus illuminating the cornea Ec of the eye E.

When the clockwise circularly polarized illumination light is reflected by the lacrimal layer of the cornea Ec, the rotating direction of the circularly polarized light is reversed. A resultant counterclockwise circularly polarized light is incident on the ¼ wave plate 7. The reflected light which is the counterclockwise circularly polarized light is converted to linear polarized light when transmitted through the ¼ wave plate 7. Since the circularly polarized light before the conversion is reversed from clockwise to counterclockwise due to reflection by the lacrimal layer, the reflected light passed through the ¼ wave plate 7 is converted to the p-polarized light having the polarization direction (axis) perpendicular to the polarization direction (axis) of the illumination light of the s-polarized light.

The reflected light converted to the p-polarized light passes through the lens 6 and is incident on the beam splitter 3. Since this reflected light have been converted to the p-polarized light, most of the reflected light is permitted to pass through the beam splitter 3 and, by an imaging lens 8, fall on an imaging face of a color CCD camera 9 that has sensitivity in light of wavelengths in the wide visible region.

On the other hand, a part of the s-polarized illumination light reflected toward the eye E by the polarization beam splitter 3 is reflected by the lens 6 toward the camera 9. This reflected light is s-polarized light as with the illumination light, so that most of the reflected light is shielded, or reflected, and is not permitted to pass through the polarization beam splitter 3. Thus, the reflected light is prevented from becoming incident on the camera 9 as a disturbance light. Accordingly, no flare occurs from the reflected light from the lens 6, that is to say, no flare is observed. The images of interference fringe formed by the lacrimal layer are produced by the camera 9 and shown on a color monitor 10. Based on the thus displayed images of interference fringes, an examiner diagnoses the eye E about the conditions of the lacrimal layer or the like.

Even if the visible light is replaced by infrared light as the illumination light, it is possible to similarly image and display the interference fringe images whereby to diagnose the examinee's eye. In this case, a CCD made for infrared light is used, and a non-color monitor may also be used. It is however preferable to use a color CCD camera that receives visible illumination light and a color monitor that displays a color image. This is because more detail diagnosis can be made based on the color or tone of the interference fringe images.

According to the ophthalmic apparatus in the above embodiment, a simple structure as above can prevent the reflected light by the back side of the objective lens from coming into incidence on the observation optical system, namely, the imaging element, thereby preventing the occurrence of flare on the observed face (imaged face). Therefore, no flare is observed in the interference fringe images formed by the lacrimal layer on the cornea displayed on the monitor, the examiner can adequately diagnose dry eye or the like based on the images of interference fringes clearly displayed on the monitor.

The ophthalmic apparatus in the embodiment can easily prevent the occurrence of flare without requiring precise optical adjustment and the like needed for arranging the polarization axes of the two polarizing plates in a perpendicular relation in the prior art apparatus.

Since the ophthalmic apparatus in the embodiment uses the polarization beam splitter for a wide visible wavelength region, the illumination light quantity and the observation light quantity can be more efficiently utilized as compared with the prior art apparatus using the half-mirror, so that three or more times the light quantity can be obtained.

As described above, according to the present invention, the occurrence of flare caused by the reflected light from the back side of the objective lens can be prevented by a simple structure. In addition, the illumination light source having a small-size and low-power can efficiently illuminate the eye to be examined. This also makes it possible to reduce load on the examinee's eye.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus for observing an eye to be examined, the apparatus including:

an observation optical system including an objective lens, for observing the eye through the objective lens;

an illumination optical system including an illumination light source, for illuminating the eye through the objective lens;

a polarization beam splitter having a property of transmitting one of linear polarized light beams that mutually perpendicularly intersect, and reflecting another linear polarized light beam, the polarization beam splitter being disposed opposite to the eye to be examined with respect to the objective lens, whereby aligning optical paths of the illumination and observation optical systems in a mutually coaxial relation; and a ¼ wave plate disposed between the objective lens and the eye to be examined.

2. The ophthalmic apparatus according to claim 1, wherein the observation optical system includes an imaging element, and the ophthalmic apparatus further includes a display unit for displaying an image imaged by the imaging element.

3. The ophthalmic apparatus according to claim 1, wherein the illumination light source includes an illumination light source that emits white illumination light, and the polarization beam splitter includes a wide wavelength region polarization beam splitter having a property of transmitting one of linear polarized light beams that have wavelengths in a wide visible region and mutually perpendicularly intersect, and reflecting another linear polarized light beam.

4. The ophthalmic apparatus according to claim 3, wherein the wide visible wavelength region includes a wavelength region of 450 to 680 nm.

5. The ophthalmic apparatus according to claim 3, wherein the observation optical system includes an imaging element having sensitivity in light having wavelengths in the wide visible region, and the ophthalmic apparatus further includes a display unit for displaying in color an image imaged by the imaging element.

6. The ophthalmic apparatus according to claim 1 further including an apparatus for observing a lacrimal layer on a cornea of the eye to be examined.

* * * * *